United States Patent
Nyman

(10) Patent No.: US 9,249,166 B1
(45) Date of Patent: Feb. 2, 2016

(54) DELAMINATED SODIUM NONATITANATE AND A METHOD FOR PRODUCING DELAMINATED SODIUM NONATITANATE

(71) Applicant: Sandia Corporation, Albuquerque, NM (US)

(72) Inventor: May D. Nyman, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/313,819

(22) Filed: Jun. 24, 2014

Related U.S. Application Data

(62) Division of application No. 13/309,708, filed on Dec. 2, 2011.

(51) Int. Cl.
  *C01G 23/00* (2006.01)
  *C07F 7/28* (2006.01)

(52) U.S. Cl.
  CPC ............... *C07F 7/28* (2013.01); *C01G 23/001* (2013.01); *C01G 23/005* (2013.01); *C01G 23/006* (2013.01)

(58) Field of Classification Search
  None
  See application file for complete search history.

(56) References Cited

U.S. PATENT DOCUMENTS

| | | | |
|---|---|---|---|
| 6,268,307 B1 * | 7/2001 | DeFilippi et al. | 502/427 |
| 7,455,826 B2 | 11/2008 | Inubushi et al. | |
| 2009/0246555 A1 * | 10/2009 | Yamamoto et al. | 428/702 |

FOREIGN PATENT DOCUMENTS

| JP | 01-267906 | | 10/1989 |
|---|---|---|---|
| JP | 2656778 JP | | 5/1997 |
| RU | 2169118 | * | 6/2001 |
| WO | 88/00090 A1 | | 1/1988 |

OTHER PUBLICATIONS

Stewart, T.A. et al., "Delaminated Titanate and Peroxotitanate Photocatalysts", Applied Catalysis B: Environmental, 105:1-2, pp. 69-76 (2011).

* cited by examiner

*Primary Examiner* — Steven Bos
(74) *Attorney, Agent, or Firm* — Daniel J. Jenkins

(57) ABSTRACT

A hydrothermal synthesis method of making a delaminated titanate is disclosed. The delaminated titanate has a unique structure or morphology. The delaminated titanate is first formed by forming at a low temperature a layered sodium nonatitanate (SNT), which may be referred to as layered sodium titanate. The layered SNT has a unique morphology. The layered SNT is then synthesized into a delaminated titanate having a unique morphology.

7 Claims, 4 Drawing Sheets

DELAMINATED SODIUM NONATITANATE AND A METHOD FOR PRODUCING DELAMINATED SODIUM NONATITANATE

CROSS-REFERENCE TO RELATED APPLICATIONS

This application is a divisional of and claims priority and benefit of U.S. patent application Ser. No. 13/309,708, "Delaminated Sodium Nonatitanate and a Method for Producing Delaminated Sodium Nonatitanate", filed Dec. 2, 2011, which is incorporated by reference herein in its entirety.

STATEMENT OF GOVERNMENT INTEREST

The United States Government has rights in this invention pursuant to Contract No. DE-AC04-94AL85000 between the United States Department of Energy and Sandia Corporation, for the operation of the Sandia National Laboratories.

FIELD

The present disclosure is generally directed to delaminated sodium titanate and a method for its production, and is more particularly directed to a hydrothermal synthesis method for producing delaminated sodium titanate having nano-sheet morphology.

BACKGROUND

Layered titanates have numerous applications including photocatalysis, coatings, paint additives, sorbents and ion-exchangers. Solid state production methods for forming layered titanates have been disclosed, for example, in Japanese Patent No. 2656778. According to these production methods, a layered titanate can be synthesized by calcinating a mixture containing carbonates, nitrates or oxides of the desired metal with titanium dioxide.

Another method of forming a layered titanic acid is disclosed in U.S. Pat. No. 7,455,826, granted Nov. 25, 2008. According to this disclosure, a solid state synthesis method is used to form a layered titanate. The process discloses 86% acidification, and has been found to require four to five twenty-four hour acidification steps to obtain 100% acidification.

The above disclosed processes require expensive starting materials and numerous processing steps.

What is needed is a method for forming a delaminated titanate that is less expensive, more effective, and requires fewer processing steps. What is further needed is a produced delaminated titanate that has higher surface area and therefore higher reactivity that would benefit many applications including, but not limited to photocatalysis and ion-exchange.

SUMMARY OF THE DISCLOSURE

In an embodiment of the present disclosure, a hydrothermal synthesis method is disclosed that includes mixing sodium hydroxide and a titanium compound to form a slurry; heating the slurry to form a layered sodium titanate having between about 15% and 30% vacancy in the titanium sites. Each layer of the layered sodium titanate has an aspect ratio of between 1:5 and 1:15.

In another embodiment of the present disclosure, a layered sodium titanate is disclosed that includes a plurality of sodium titanate layers layered upon one another. Each layer of the titanate layers has an aspect ratio of between 1:5 and 1:15.

In another embodiment of the present disclosure, a layered acid titanate is disclosed that includes a plurality of acid titanate layers layered upon one another. Each layer of the acid titanate layers has an aspect ratio of between 1:5 and 1:15.

In another embodiment of the present disclosure, a delaminated titanate is disclosed that includes a plurality of titanate planks in a solution. Each titanate plank has an aspect ratio of between 1:5 and 1:15.

In another embodiment of the present disclosure, a layered delaminated titanate is disclosed that includes a plurality of delaminated alkyl ammonium titanate or delaminated alkyl phosphonium titanate layers layered upon one another. Each layer of the plurality of delaminated alkyl ammonium titanate or delaminated alkyl phosphonium titanate layers has an aspect ratio of between 1:5 and 1:15.

One advantage of the present disclosure is to provide a method for producing a delaminated sodium nonatitanate that has improved surface area for applications requiring this such as photocatalysis and ion-exchange.

Other features and advantages of the present disclosure will be apparent from the following more detailed description of the preferred embodiment, taken in conjunction with the accompanying drawings which illustrate, by way of example, the principles of the disclosure.

BRIEF DESCRIPTION OF THE DRAWINGS

Wherever possible, the same reference numbers will be used throughout the drawings to represent the same parts.

DETAILED DESCRIPTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete and will fully convey the scope of the invention to those skilled in the art.

Figure 1:
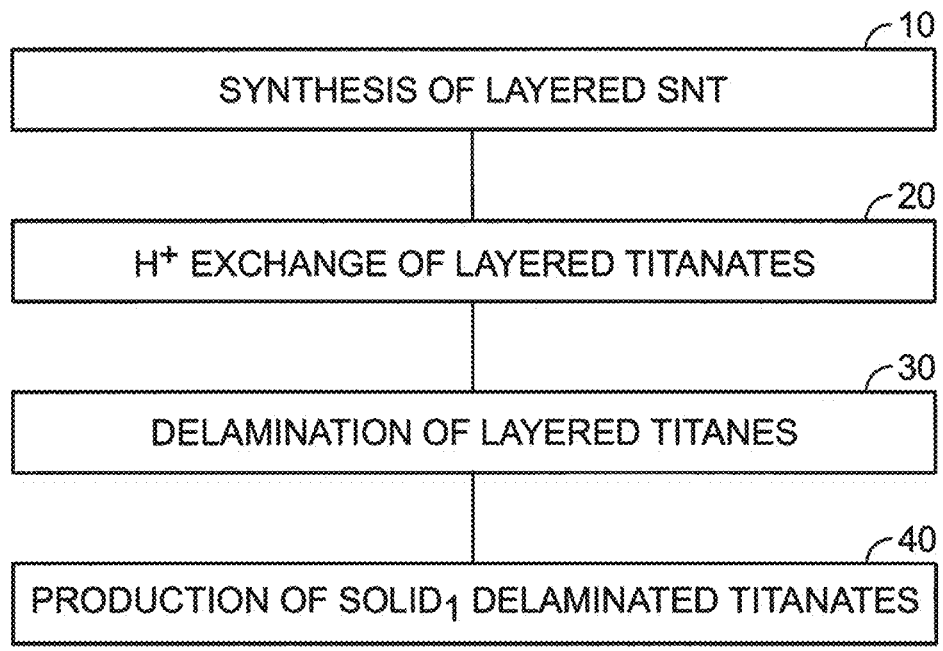
FIG. 1 is a flow chart illustrating an embodiment of a process for forming a delaminated titanate according to an embodiment of the present disclosure.

According to an embodiment of the present invention, a hydrothermal synthesis method of making a delaminated titanate is disclosed. The delaminated titanate has a unique structure or morphology. The delaminated titanate is first synthesized by forming a layered sodium nonatitanate (SNT), which may be referred to a as layered sodium titanate, having a unique morphology. The layered SNT is then converted into a layered acid titanate having a unique morphology. Finally, the layered acid titanate is then converted into a delaminated alkyl ammonium or alkyl phosphonium titanate having a unique morphology. The morphology of the layered or delaminated titanates formed by the process of the present disclosure includes an unexpected aspect ratio of between about 1:5 and 1:15, in surprising contrast to layered or delaminated CsTi., which have an aspect ratio of about 1:1. The process is generally shown in the flow chart and illustrated process diagram of FIG. 1 and FIG. 2, respectively.

According to the first step 10, a layered SNT 200 is formed by a hydrothermal synthesis process according to the present invention. The hydrothermal synthesis begins by first dissolving sodium hydroxide (NaOH) in water to make a sodium hydroxide solution. An amount of titanium is then added to the sodium hydroxide solution while stirring vigorously. The titanium may be provided as titanium (IV) alkoxide or chloride. In an embodiment, the alkoxide may be a methoxide, ethoxide, propoxide, or other similar group. A white slurry is formed that includes hydrous titania suspended in water.

The hydrous titania suspension is heated to a temperature between about 100° C. and about 170° C. for a sufficient time to dissolve the hydrous titania and form crystallized layered sodium titanate (layered SNT) 200 having the general formula Na.53Ti0.8O1.73(OH)0.27.0.76H2O. In another embodiment, the hydrous titania is heated to a temperature between about 150° C. and about 170° C. In another embodiment, the hydrous titania is heated to a temperature of about 170° C. In an embodiment, the hydrous titania is heated for about 5 days. The sodium titanate is then collected by pressure filtration, vacuum filtration or other separation technique.

Figure 2:
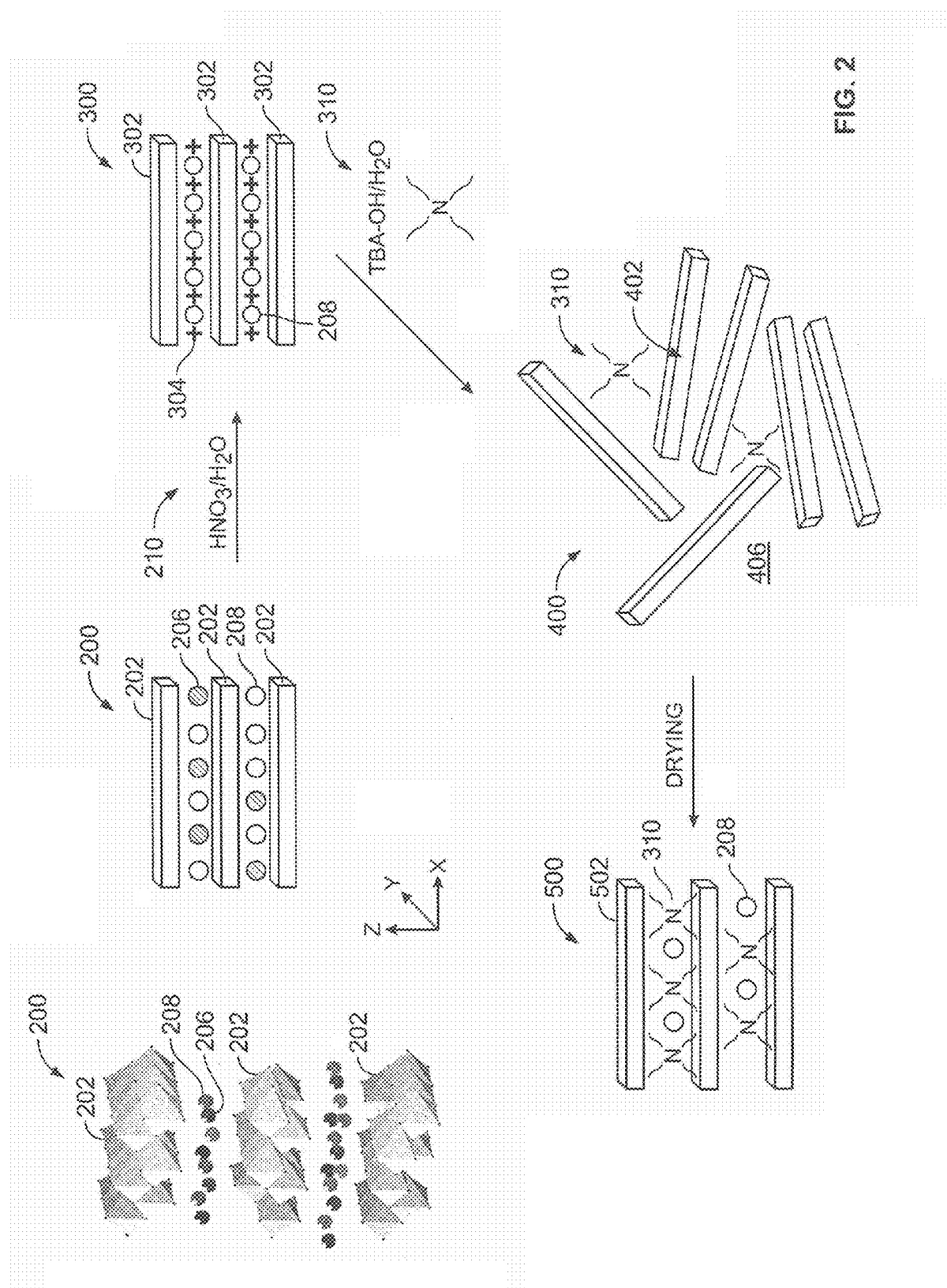
FIG. 2 is an illustrated process diagram according to an embodiment of the present disclosure.

As can be seen in FIG. 2, the layered sodium titanate 200 is a double-layer of edge-sharing TiO6 octahedra 202, with between about 15% and about 30% of the Ti sites 112 vacant. In another embodiment, approximately 20% of the Ti sites 204 are vacant. The sodium 206 and water 208 reside between the double-layer of TiO6 octahedra 202.

The layered sodium titanate 200 in FIGS. 2(a) and 2(b) is shown including three layers of titanate 202 for illustrative purposes. The layered sodium titanate produced by the disclosed method includes between about 10 and about 50 layers of titanate 200 within a single coherent crystal or grain of sodium titanate. Each layer 202 has an aspect ratio in both the Y:X axis of between about 1:5 and about 1:15. In an embodiment, each layer 202a has a Y:X aspect ratio of about 1:10. The layers 202 may be referred to as having a "plank" geometry. This is in contrast to the prior art CsTi, which has a Y:X aspect ratio of about 1:1, which may be referred to as a "sheet" geometry. The Z thickness of the planks of the present disclosure are about 5 Å. The Z:X ratio of the titanate planks of the present disclosure are about 1:200 to about 1:600, which is similar to the prior art plate geometry.

According to a second step 20 (FIG. 1), which may be referred to as a H+-exchange or acid exchange step, and referring again to FIG. 1, sodium is replaced with H3O+ to form a layered acid titanate 300, (H3O+)0.53Ti0.8O1.73 (OH)0.27.xH2O. (x may vary between 0.5 and 2). The driving force of the exchange is neutralization: H++OH−=H2O. In this step, proton exchange for Na is carried out with a strong acid 210. The strong acid 210 may be selected from the group including, but not limited to nitric acid, hydrochloric acid and sulfuric acid. In an embodiment, the acid may be nitric acid. In an embodiment, the acid may be a 1 M HNO3 solution. In these exchange conditions, neither layered phase is observed to undergo any dissolution. The H+-exchanged powder is then collected. In an embodiment, the H+-exchanged powder may be collected by centrifugation and washing. In an embodiment, the washing step may include first washing with water then alcohol. Completeness of exchanged may be checked by either energy dispersive spectroscopy, or thermogravimetry to 90° C., followed by X-ray diffraction of the heat-treated powder. If Na remained, sodium titanate phases would be observed in the diffraction pattern. If the Na was completely removed, only TiO2 will be observed. The acid-exchange of SNT was completed i.e. no sodium remaining, in a single step, or in other words, the reaction is driven to 100% completion.

As can be seen in FIG. 2, the layered acid titanate 300 produced by the disclosed method is a double-layer of edge-sharing TiO6 octahedra 302, with between about 15% and about 30% of the Ti sites 312 vacant. In another embodiment, approximately 20% of the Ti sites 312 are vacant. H3O+ 304 and water 208 reside between the double-layer of TiO6 octahedra 302.

The purpose of the second step 20 (FIG. 1) is to make the layered titanate more reactive for exchange with large cations such as tetrabutylammonium hydroxide (TBA), used in the third step 30.

According to a third step 30 (FIG. 1), which may be referred to as a delamination step, $H_3O^+$ is replaced with $NR_4^+$ (alkyl ammonium) or $PR_4^+$ (alkyl phosphonium) to form a delaminated titanate 400 of the form delaminated alkyl ammonium titanate, $(NR_4^+)_{0.53}Ti_{0.8}O_{1.73}(OH)_{0.27}.xH_2O$ (x may vary between 0.5 and 2), or delaminated alkyl phosphonium titanate, $(PH_4^+)_{0.53}Ti_{0.8}O_{1.73}(OH)_{0.27}.xH_2O$ (x may vary between 0.5 and 2), which both forms may be referred to as delaminated SNT 400. The purpose of this step is to delaminate the titanate layers 302, so the $NR_4^+$ needs to be large. The $NR_4^+$ drives the titanate layers 402 apart so they can form a stable aqueous colloid of individual titanate layers 402, not associated with each other. Their exact state as a colloid is not entirely known, but likely the $NR_4^+$ are loosely associated with the titanate planks 402 in the aqueous medium.

The third step 30 is performed by adding a delaminating agent 310 to the layered acid titanate 300. The delaminating agent 310 may be a hydroxide of alkyl ammonium or alkyl phosphonium. The base may be any NR4+ or PH4+, where R is any large alkyl (i.e. butyl, pentyl, hexyl, etc.), alkyl substituted with functional group such as a carboxylate or sulfate. The alkyl can be branched or straight chain, and not all alkyls need to be identical for example, trimethyl-dodecyl ammonium hydroxide. In an embodiment, the base may be tetrabutylammonium hydroxide (TBA).

The delaminating agent and the H+-titanate powders are combined and mixed for a period of time sufficient to replace the H3O+ with the alkyl ammonium or alkyl phosphonium. In an embodiment, the mixing time may be about 40 minutes. The exchange is complete to 100% after one performance of the third step.

As can be seen in FIG. 2, the delaminated titanate planks 402 are no longer associated with one another, and present in and aqueous medium 406 including the delaminating agent 310.

The delaminated titanate 400 in aqueous medium 406 produced in the third step may then be dried in an optional fourth step 40 (FIG. 1) to produce a delaminated layered titanate 500, (NR4+)0.53Ti0.8O1.73(OH)0.27.xH2O (x between 0.2 and 2) or (PH4+)0.53Ti0.8O1.73(OH)0.27.xH2O (x between 0.5 and 2). The solid, delaminated layered titanate 500 may be formed and isolated by centrifugation, washing and drying, or other separation/drying technique. In an embodiment, the drying may be performed in a vacuum oven at about 70° C. to about 90° C.

The delaminated layered titanate 500 includes a plurality of layers of delaminated titanate 502. The delaminated titanate layers 502 are separated by a greater distance than the layers of sodium titanate 202 in the layered SNT 200. Between the titanate layers 502 is the delaminating agent 310 and water 208. In an embodiment, the delaminating agent 310 may be alkyl ammonium or alkyl phosphonium.

The following example is intended to be illustrative of the present invention, but is not intended to limit the claimed invention.

Example 1

A delaminated titanate was formed according to the preceding process steps. According to the first step, SNT was synthesized hydrothermally by dissolving approximately 10 grams (0.25 mol) of sodium hydroxide (NaOH) in 48 mL of distilled water in a 125 mL Teflon® liner for a Parr reactor. Titanium (IV) isopropoxide (9.6 g, 0.033 mol) was added while stirring vigorously. A white slurry formed. The reactor was closed and placed in a 170° C. oven for five days. Approximately 4 g of white powder product was collected by pressure filtration.

According to the second step, proton exchange for Na was carried out with 1 M HNO3 solution, utilizing a Turbula®, which is a high powered shaker that rotates on three axes, operated for one hour. Four grams of alkali titanate were combined with 75 mL of nitric acid in a Teflon® bottle. In these exchange conditions, neither layered phase is observed to undergo any dissolution. The H3O+-exchanged powder was collected by centrifugation and washing; first with water then alcohol. Completeness of exchanged was checked by either energy dispersive spectroscopy, or thermogravimetry to 900° C., followed by X-ray diffraction of the heat-treated powder. If Na remained, sodium titanate phases would be observed in the diffraction pattern. Only TiO2 was observed, indicating that Na was completely removed. The acid-exchange of SNT was completed in a single one-hour step. This is in sharp, unexpected contrast to the prior art that forms layered Cs titanate requiring 4 to 5, 24 hour exchange steps.

According to a third step, a 40 wt. % tetrabutylammonium hydroxide (TBA) aqueous solution was diluted by approximately 50% with water; and the H+-titanate powders combined with the solution for Turbula® treatment for approximately 40 minutes. Both materials only required one step for complete exchange. The solid, delaminated layered SNT was isolated by centrifugation, washing and finally drying in a vacuum oven at 70° C. to about 90° C.

Figures 3, 4:
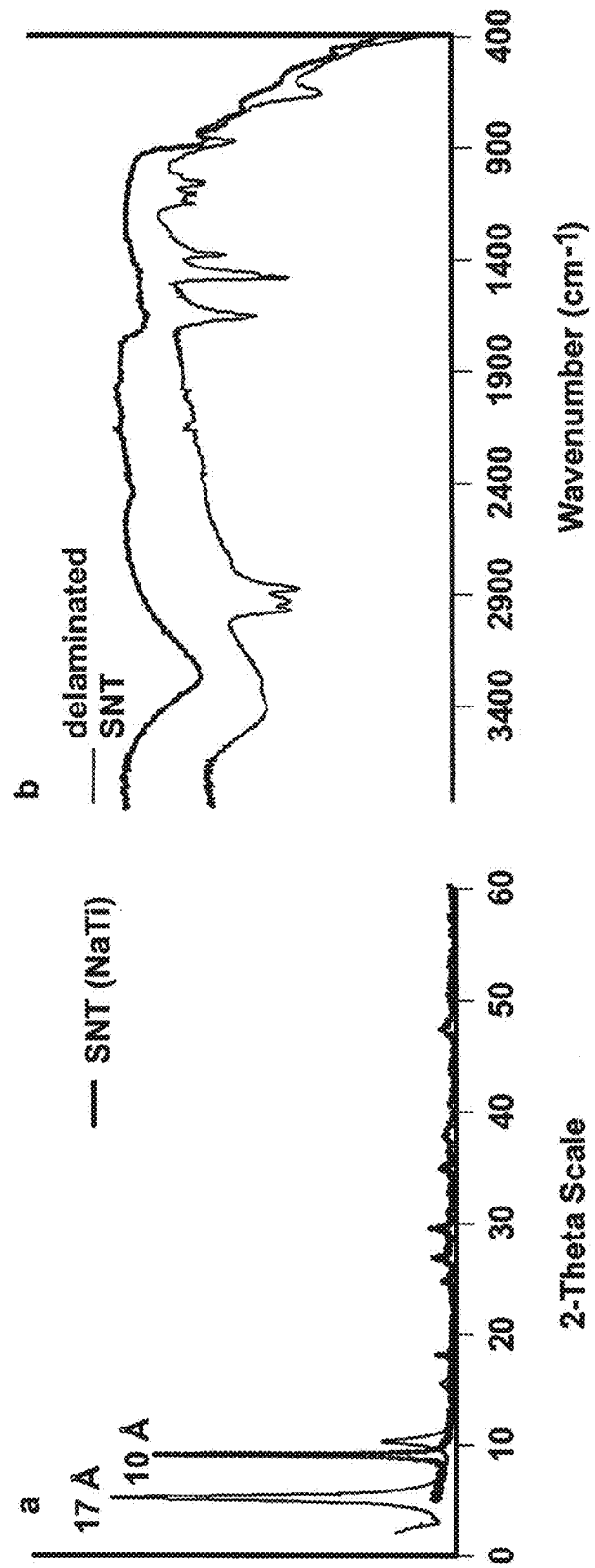
FIG. 3 is an X-ray diffraction of layered SNT and TBA-delaminated titanate according to an embodiment of the present disclosure.
FIG. 4 is an infrared spectrum of layered SNT and TBA-delaminated titanate according to an embodiment of the present disclosure.

FIG. 3 shows X-ray diffraction spectra of layered SNT and solid, TBA-delaminated SNT according to the present disclosure. The SNT has a d-spacing of approximately 10 Å while the TBA-delaminated SNT has a layer-spacing of approximately 17 Å. The titania layers remain the same thickness throughout the process. The change in d-spacing that is observed is related to the size of what resides between the layers. The sodium and water are smaller than the TBA, so increase in the d-spacing indicates exchange.

FIG. 4 shows the infrared spectra of layered SNT and solid, TBA-delaminated SNT (the materials of FIG. 3), clearly showing the vibrations of the TBA-cation for the delaminated SNT.

The use of colloidal suspensions of the titanate nanosheets is convenient for screening experiments utilizing different materials, conditions and contaminants in photocatalysis studies, one use of titanate layers; but surface-bound titanates have greater potential for practical use in remediating organic and microbial contamination in water. Furthermore, the delaminated titanate layers have the ideal morphology for adsorption onto a flat surface. Coupling agents were explored for the purpose of affixing the titanate layers to high-quality mica surfaces (specifically for AFM characterization). The titanate layers are anionic under most pH conditions, and cations were considered that would adhere readily to the anionic mica surface when deposited from an aqueous solution. While organic cations, such as polymers, can be utilized, they might themselves be vulnerable to catalytic photo-oxidation. Therefore, inorganic polycations were used. Specifically, Ga-centered aluminum cluster, [GaO4 Al12 (OH)24 (H2 O)12]7+, GaAl12 was used as the "cationic glue."

Figure 5:
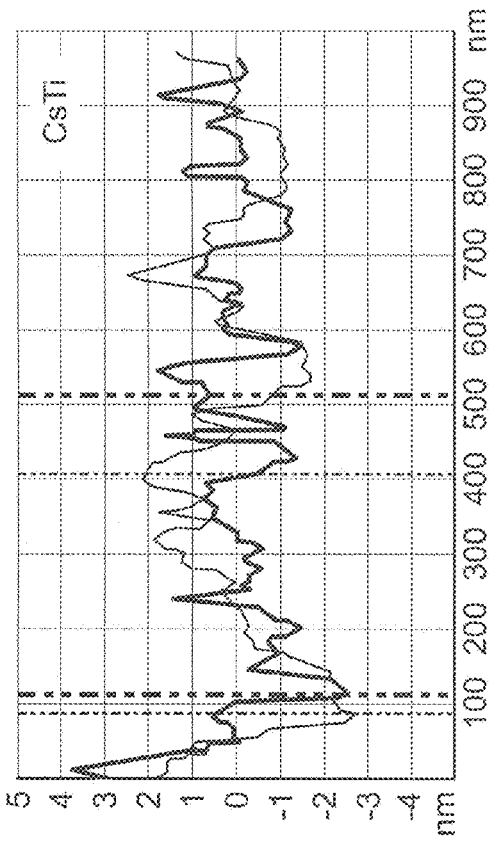
FIG. 5 is an AFM image and corresponding height profile of delaminated layers derived from Cs titanate.
Figure 6:
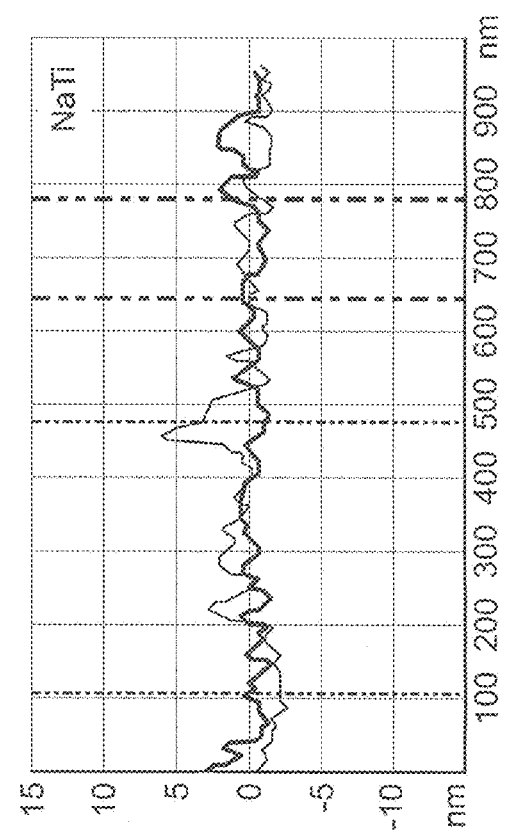
FIG. 6 is an AFM image and corresponding height profile of delaminated layers derived from Na titanate according to an embodiment of the present disclosure.

Dense coverages of delaminated titanate from prior art CsTi and NaTi according to the disclosure, were assembled on GaAl12 coated mica surfaces. The CsTi and NaTi coatings imaged by AFM are shown in FIG. 5 and FIG. 6, respectively. Morphological differences are clearly apparent. Qualitatively, the CsTi derived coatings are more sheet-like, whereas the NaTi layers can be described as more fibrous or plank-like. This is in agreement with prior art CsTi disclosures that report an aspect ratio of delaminated CsTi as about 1:1. Height profiles are shown for each image. The maximum height difference is 4 nm for both the CsTi and NaTi layers. The double-layer of edge-sharing TiO6 octahedra of the both titanate phases is approximately 0.4 nm thick; and the GaAl2 polycation is approximately 1 nm in diameter. Therefore, the dense layers shown in FIG. 5 and FIG. 6 are fewer are than 10 titania-layers thick. It is not clear from these studies if TBA resides between some co-adsorbed titania layers.

While the disclosure has been described with reference to a preferred embodiment, it will be understood by those skilled in the art that various changes may be made and equivalents may be substituted for elements thereof without departing from the scope of the disclosure. For example, telescoping or linear devices may be hydraulically driven, and/or these devices may be driven with hydraulics, air, water, or electricity or any combination thereof.

In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A hydrothermal synthesis method, comprising:
   mixing sodium hydroxide and a titanium compound to form a slurry;
   heating the slurry to form a layered sodium titanate having between about 15% and 30% vacancy in the titanium sites;
   adding an acid to the layered sodium titanate to form a layered acid titanate; and
   adding a hydroxide of an alkyl ammonium or alkyl phosphonium to the layered acid titanate to form a delaminated titanate consisting of titanate layers;
   wherein each layer of the layered sodium titanate has an aspect ratio of between 1:5 and 1:15.

2. The method of claim 1, wherein the heating is between 150° C. and 170° C.

3. The method of claim 1, wherein the amount of vacancy in the titanium sites is about 20%.

4. The method of claim 1, wherein the heating is at about 170° C.

5. The method of claim 1, further comprising:
   drying the delaminated titanate to form a dried delaminated titanate.

6. The method of claim 5, wherein the delaminated titanate is selected from the group consisting of a delaminated alkyl ammonium titanate and delaminated alkyl phosphonium titanate.

7. The method of claim 5, wherein forming the delaminated titanate comprises mixing the layered acid titanate with tetrabutylammonium hydroxide.

* * * * *